(12) United States Patent
Verenchikov

(10) Patent No.: US 10,006,892 B2
(45) Date of Patent: Jun. 26, 2018

(54) METHOD OF TARGETED MASS SPECTROMETRIC ANALYSIS

(71) Applicant: LECO Corporation, St. Joseph, MI (US)

(72) Inventor: Anatoly N. Verenchikov, St. Petersburg (RU)

(73) Assignee: LECO Corporation, St. Joseph, MI (US)

( * ) Notice: Subject to any disclaimer, the term of this patent is extended or adjusted under 35 U.S.C. 154(b) by 0 days. days.

(21) Appl. No.: 15/301,129

(22) PCT Filed: Oct. 23, 2014

(86) PCT No.: PCT/US2014/061945
§ 371 (c)(1),
(2) Date: Sep. 30, 2016

(87) PCT Pub. No.: WO2015/152968
PCT Pub. Date: Oct. 8, 2015

(65) Prior Publication Data
US 2017/0016863 A1 Jan. 19, 2017

Related U.S. Application Data

(60) Provisional application No. 61/972,998, filed on Mar. 31, 2014.

(51) Int. Cl.
*G01N 30/72* (2006.01)
*H01J 49/14* (2006.01)
(Continued)

(52) U.S. Cl.
CPC ...... *G01N 30/7206* (2013.01); *H01J 49/0031* (2013.01); *H01J 49/147* (2013.01); *H01J 49/401* (2013.01); *H01J 49/406* (2013.01)

(58) Field of Classification Search
CPC ............. G01N 30/7206; H01J 39/0031; H01J 39/147; H01J 39/406; H01J 39/401
See application file for complete search history.

(56) References Cited

U.S. PATENT DOCUMENTS

| 6,111,250 A | 8/2000 | Thomson et al. |
| 2003/0155497 A1* | 8/2003 | Kato ................ H01J 49/0031 250/281 |

(Continued)

FOREIGN PATENT DOCUMENTS

| CN | 103069539 A | 4/2013 |
| JP | 2003223864 A | 8/2003 |

(Continued)

OTHER PUBLICATIONS

Office Action for the related Chinese Application No. 201480078713.8 dated Jul. 20, 2017 with its English translation.

(Continued)

*Primary Examiner* — Eliza Osenbaugh-Stewar
(74) *Attorney, Agent, or Firm* — Honigman Miller Schwartz and Cohn LLP

(57) ABSTRACT

A method of targeted mass spectrometric analysis is provided for analyzing trace compounds at sub-ppb level compared to sample matrix. Sample is chromatographically separated at standard conditions to employ a map of target mass (M) versus retention time (RT). Small mass ions under M(RT) are rejected by RF field, and remaining ions are accumulated for pulsed injection into a multi-reflecting TOF MS, either directly from EI source, or from linear RF trap or via a heated RF only quadrupole with axial ion trapping. In combination with EI source the method provides sub femtogram sensitivity at matrices loads in microgram range.

11 Claims, 11 Drawing Sheets

(51) Int. Cl.
*H01J 49/40* (2006.01)
*H01J 49/00* (2006.01)

(56) References Cited

U.S. PATENT DOCUMENTS

| | | | |
|---|---|---|---|
| 2005/0063864 A1* | 3/2005 | Sano | G01N 33/6848 422/68.1 |
| 2005/0211891 A1 | 9/2005 | Belov et al. | |
| 2013/0056627 A1* | 3/2013 | Verenchikov | H01J 49/406 250/282 |
| 2013/0206978 A1 | 8/2013 | Verenchikov et al. | |

FOREIGN PATENT DOCUMENTS

| | | |
|---|---|---|
| JP | 2010014563 A | 1/2010 |
| WO | WO-2005001878 A2 | 1/2005 |
| WO | WO-2012/024468 A2 | 2/2012 |

OTHER PUBLICATIONS

International Search Report dated Jan. 13, 2015, relating to International Application No. PCT/US2014/061945.
March, R. E., "An Introduction to Quadrupole Ion Trap Mass Spectrometry", Journal of Mass Spectrometry, vol. 32, No. 4, Apr. 1, 1997, pp. 351-369, Wiley, Chichester, GB.
Japanese Office Action for the related Japanese Application No. 2016-560572 dated Oct. 4, 2017.

* cited by examiner

Fig.1: PRIOR ART

METHOD OF TARGETED MASS SPECTROMETRIC ANALYSIS

CROSS-REFERENCE TO RELATED APPLICATIONS

This application claims priority under 35 U.S.C. § 371 to Patent Cooperation Treaty Application No. PCT/US2014/061945, filed Oct. 23, 2014, which claims priority under 35 U.S.C. § 119(e) to U.S. Provisional Application No. 61/972,998, filed Mar. 31, 2014. The disclosures of these prior applications are considered part of the disclosure of this application and are hereby incorporated by reference in their entireties.

BACKGROUND

Electron impact (EI) ionization is widely employed for environmental analysis and technological control. Samples of interest are extracted from analyzed media, like food, soil or water. The extracts contain impurities of interest within rich chemical matrixes. The extracts are separated in time within single or two-dimensional gas chromatography (GC or GC×GC). A GC carrier gas, typically Helium, delivers the sample into an EI source for ionization by an electron beam. Electron energy is generally kept at 70 eV in order to obtain standard fragment spectra. Spectra are submitted for comparison with a library of standard EI spectra for identification of compounds.

Many applications demand analysis of ultra traces at high level of sensitivity (e.g., at least under 1 pg and preferably at 1 fg level) and with a high dynamic range (e.g., at least 1E+5 and desirably at 1E+9) between ultra traces and rich chemical matrix. Data with high resolving power is generally sought for reliable compound identification and for improving a ratio of signal to chemical noise.

Many GC-mass spectrometer systems employ quadrupole analyzers. Since EI spectra contain a multiplicity of peaks, it is generally necessary to use a scan mass analyzer over a wide mass range, which leads to inevitable ion losses, slows down spectra acquisition, and introduces skew in the shape of individual mass traces, distorting fragment intensity ratios. Since GC and in particular GC×GC separation provide short chromatographic peaks (e.g., under 50 ms in GC×GC case), a Time-of-flight mass spectrometer (TOF MS) is generally used for rapid acquisition of panoramic (full mass range) spectra.

To separate target compounds of close isobars of matrix ions and their low abundant isotopes it is desirable to employ high resolution mass spectrometers, such as multi-reflecting TOF MS (MR-TOF MS). As example, separating a pair of $^{13}C$ from $^{12}CH$ with 4.5 mDa mass difference for ions with mass 300 requires 75,000 resolution. For dioxin analysis the required resolution is 10,000 at 10% peak height and for some toxic benzo-furans resolution should exceed 18,000.

WO2012024468, incorporated herein by reference, describes a method of ion storage within an electron beam of so-called "closed" EI source followed by synchronized release into an orthogonal accelerator (OA) for ultra-sensitive analysis (LOD=1 fg) in MR-TOF at high resolution in excess of 30,000. However, the EI storage capacity tends to saturate by space charge when trace compounds are analyzed within concentrated matrices at momentarily sample fluxes in excess of 1 ng/sec, thus limiting the detectable threshold of relative sample concentration per matrix above 10 ppb (parts per billion). To bypass the limitation, a laborious sample preparation is required. Thus, a lower detection threshold is desired for analysis of highly toxic compounds such as pesticides in baby food or dioxins in environmental samples.

SUMMARY

In general, an improved method of trace mass spectrometric analysis is described. The method primarily employs gas chromatographic separation, electron impact ionization, and mass analysis in multi reflecting time-of-flight mass spectrometer. An improvement is achieved due to ion beam spatial compression within a heated RF only quadrupole (RFQ), removal of vast majority of ion flux with low mass cut-off in RFQ, ion storage in RFQ at strongly reduced space charge and pulsed ion ejection into a synchronized orthogonal accelerator, such that to admit relatively narrow target mass range at maximized efficiency of ion injection into the accelerator. Advantageously, the disclosed spectrometer improves the combination of resolution, sensitivity and dynamic range in such method due to substantial reduction of ionic space charge within the RFQ, extending size of ion storage region compared to storing EI source, and by spatial focusing of ion packets within the relatively short orthogonal accelerator of MR-TOF, thus bringing efficiency of pulsed conversion close to unity. Contrary to other types of MS analyses, selection of narrow mass range becomes an advantage since it does not affect sensitivity for target compounds with known map of molecular mass Vs chromatographic retention time (RT). At the same time, rejection of unwanted ions strongly reduces space charge within RFQ, so as detector load. The method is also applicable to other types of ion sources, such as CI, APPI, APCI, conditioned GD, and SESI, preferably providing selective and soft ionization for maximizing signal of target molecular ions. Preferably, resolution of MR-TOF is improved by employing so-called zoom mode, applicable for reduced mass ranges.

The details of one or more implementations of the disclosure are set forth in the accompanying drawings and the description below. Other aspects, features, and advantages will be apparent from the description and drawings, and from the claims.

DESCRIPTION OF DRAWINGS

Various embodiments of the present invention together with arrangement given illustrative purposes only will now be described, by way of example only, and with reference to the accompanying drawings in which.

Like reference symbols in the various drawings indicate like elements.

DETAILED DESCRIPTION

Figure 1:
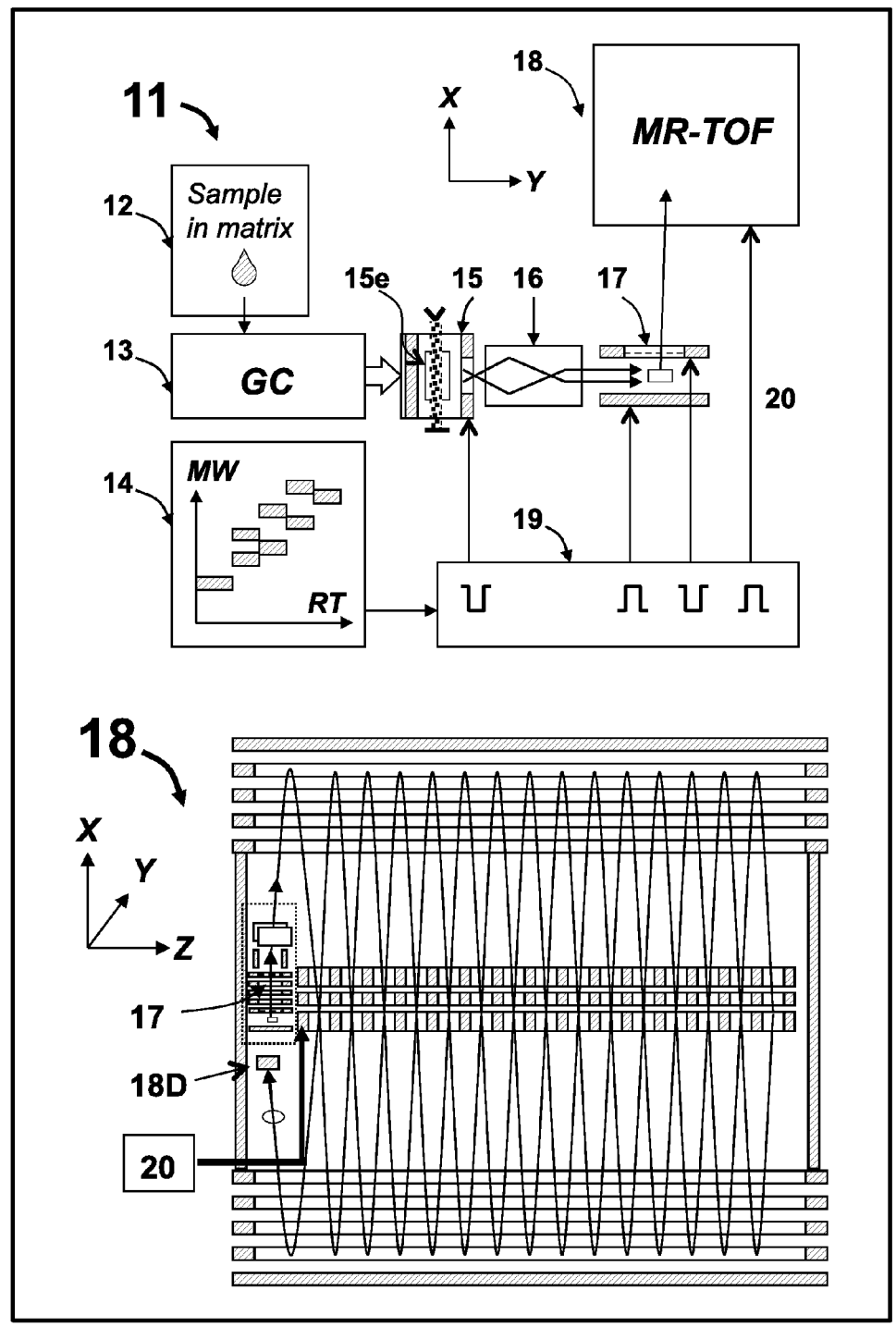
FIG. 1 is a schematic view of prior art exemplary MR-TOF mass spectrometer system with accumulating EI source.

FIG. 1 provides a schematic view of a (WO2012024468) MR-TOF MS system 11 employing a gas chromatograph 13, an ion accumulating electron impact (EI) ionization source 15, a transfer ion optics 16, a synchronized orthogonal accelerator 17 (OA), and an MR-TOF analyzer 18.

The system is primarily suited for targeted mass analysis, wherein an ultra small (sub-pg to low fg) amount of sample is to be detected in the presence of a sample matrix, naturally remaining at sample preparation and concentration steps. Molecular mass or major peak mass, such as chromatographic retention times (RT) are known from prior experiments with injection of standards, which allows generating an M(RT) map for every particular targeted analysis. The EI source accumulates ions within the potential well of a strong (1-3 mA) electron beam. Periodically and synchronized with OA the stored ions are pulse ejected from the EI source by pulses from a generator 19, applied to EI electrodes. Extraction pulses are also applied to OA with a time delay, pre-calculated for target mass M(RT). The OA admits relatively narrow mass range, typically 20-30 amu wide, just sufficient to record spectra of both—target compound and of isotope diluted standards. To reduce saturation of space charge in the EI source, the extraction pulses may be applied at a time period that is notably shorter than the flight time in the MR-TOF. Alternatively, pulses may be applied at longer period and MR-TOF is operated in a zoom mode. Zoom mode in MR-TOF 18 is usually arranged by applying pulsed deflection 20 to side lens elements of MR-TOF, thus pushing ions for another full pass within the analyzer for increasing MR-TOF resolution.

The exemplar EI-MR-TOF allows ultra-sensitive analysis, however, only at a condition of limited matrix concentration. At slow pulsing (once per 1 ms) the EI source saturates at neutral flux of at or around 30-100 pg/s and at faster pulsing (about once per 30 us) at about 1 ng/sec matrix fluxes. Accounting for 10-30 min GC runs, this corresponds to approximately a 100 ng limit of the overall matrix amount, i.e. the analysis is limited to at or around 10 ppb (1E-8) relative concentration of targeted compounds. The achievement is excellent, but may not be sufficient for more demanding applications. The desired level of dioxin analysis is down to 1 ppq (1E-15), while sample pre-concentration is known to be limited to 1E+5 to 1E+6. Thus, it is desired to achieve yet lower limit for detectable relative concentration.

The inventors realized that the vast majority of accumulated ions are of low mass under about 100-150 amu. Such low mass ions are responsible for most of the space charge saturation in the ion storage region, while target masses are above this threshold. As an example, toxic dioxins are within about 300 to 500 amu.

Figure 2:
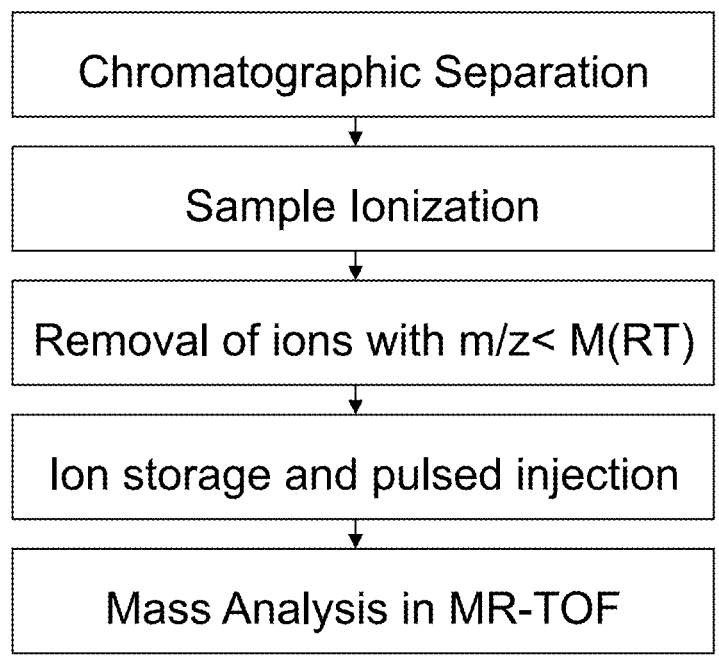
FIG. 2 is a schematic block diagram of the provided method of trace mass spectrometric analysis.

Referring mpw to FIG. 2, in the most general form, the proposed method of targeted mass spectrometric analysis comprises the following steps: (a) chromatographic separation at standard conditions such that masses of target compounds are mapped as a function of chromatographic retention times M (RT); (b) sample ionization; (c) removal of low mass ions smaller than m(RT); (d) ion accumulation and pulsed ejection either in electron beam, or radiofrequency quadrupole or RF trap; and (d) mass analysis in multi-reflecting time-of-flight mass spectrometer MR-TOF MS or electrostatic traps. In an implementation, preferably, the method may further comprise a step of synchronized orthogonal acceleration. Multiple details of the method and its variants are further illustrated for particular apparatuses. Here it is worth commenting that the method primarily deals with improvement of ion storing and rare pulse ejection, so some of the method advantages are applicable to a more generalized group of electrostatic analyzers with extended mass analysis time, such as multi-reflecting TOF MS, multi-turn TOF MS, open electrostatic traps, electrostatic traps with FT analysis and orbital traps.

Figure 3:
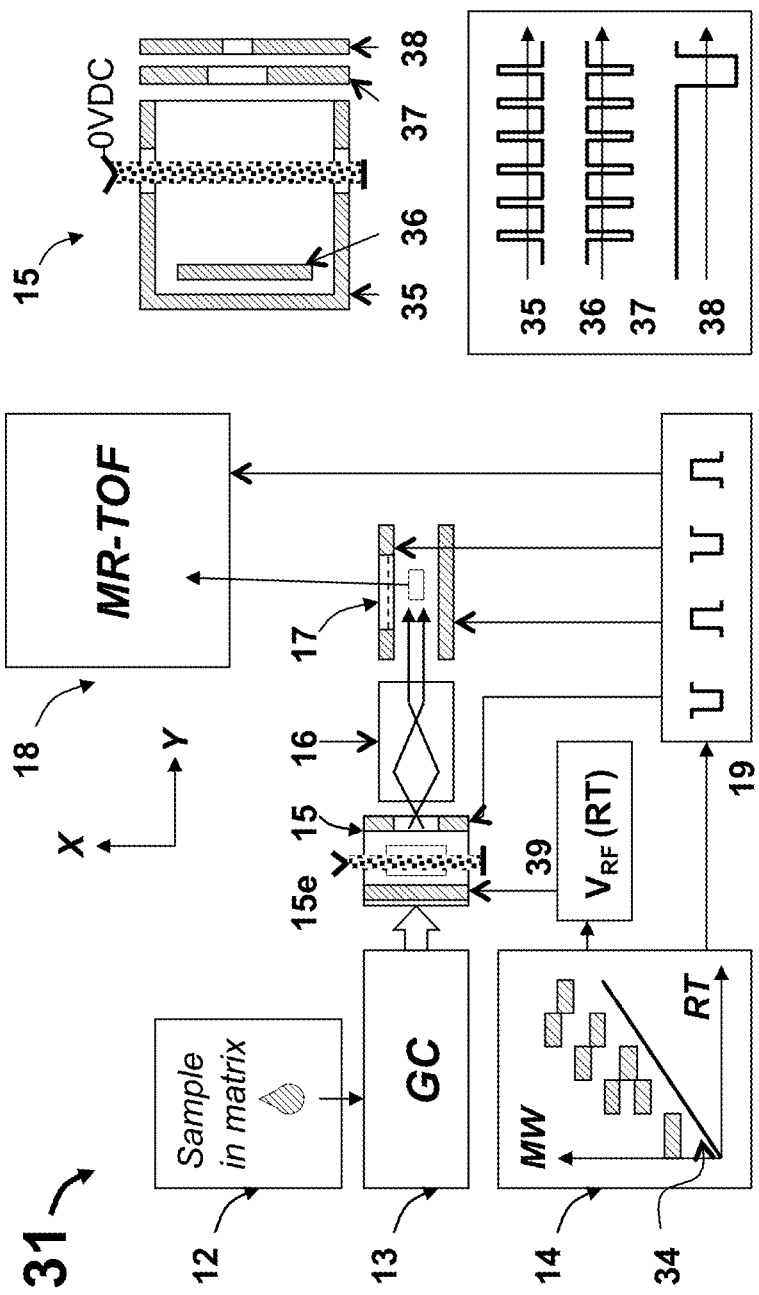
FIG. 3 is a schematic view of an EI-MR-TOF system with ion filtering and ion accumulation in a EI ion source.

FIG. 3 provides a schematic view of an EI-MR-TOF system 31 with ion filtering and ion accumulation in EI ion source, according to an implementation. The system 31 is different from system 11 by adding a periodic pulsed or an RF signal 39 to at least one electrode of EI source 15. In the shown example, a periodic pulsed signal in the frequency range of at or about 0.3-3 MHz and at or about 50-100V amplitude is applied to ion chamber 35 and a generally symmetric and opposite polarity pulsed signal is applied to electrodes 36 and 37. Symmetric DC biases are provided to electrodes 36-37 to return large mass ions to the center of thus formed quadrupolar trap, while small mass ions will be removed from the trap. The low mass cut-off may be adjusted with retention time (RT) by adjusting either amplitude or frequency of the pulsed signal according to curve 34 in M(RT) plot 14, i.e. below mass of target compounds at any particular RT. Also note that due to signal symmetry and due to proper choice of electrode distance per chamber diameter (distance is approximately 0.9 of diameter) the net potential at the center of the trap is not affected by pulsed signals and DC bias on electrodes 36-37. Since about 70 eV electrons fly through about a 1 cm source in at or around 2 ns time, electron beam will experience time modulation, however, without losing ion trapping properties. At completion of ion storage within a period of at or about 100 us-1 ms, an extracting pulse is applied to extraction electrode 38 to extract stored ions into a synchronized OA 17. Optionally, pulsed signals may be switched off or driven to one state at extraction time. Optionally, electron beam may be blocked by negative bias of signal 35 at ion extraction time. Optimal arrangement of signals is yet to be determined in experiments.

Removal of light ions dramatically (by about 2-3 orders of magnitude for cut off mass at or around 100-150 amu) reduces space charge of accumulated ions, which tends to preserve accumulating properties of EI source at substantially increased sample loads up to at or around 10 ng/sec limit of GC micro-column capacity.

Figure 4:
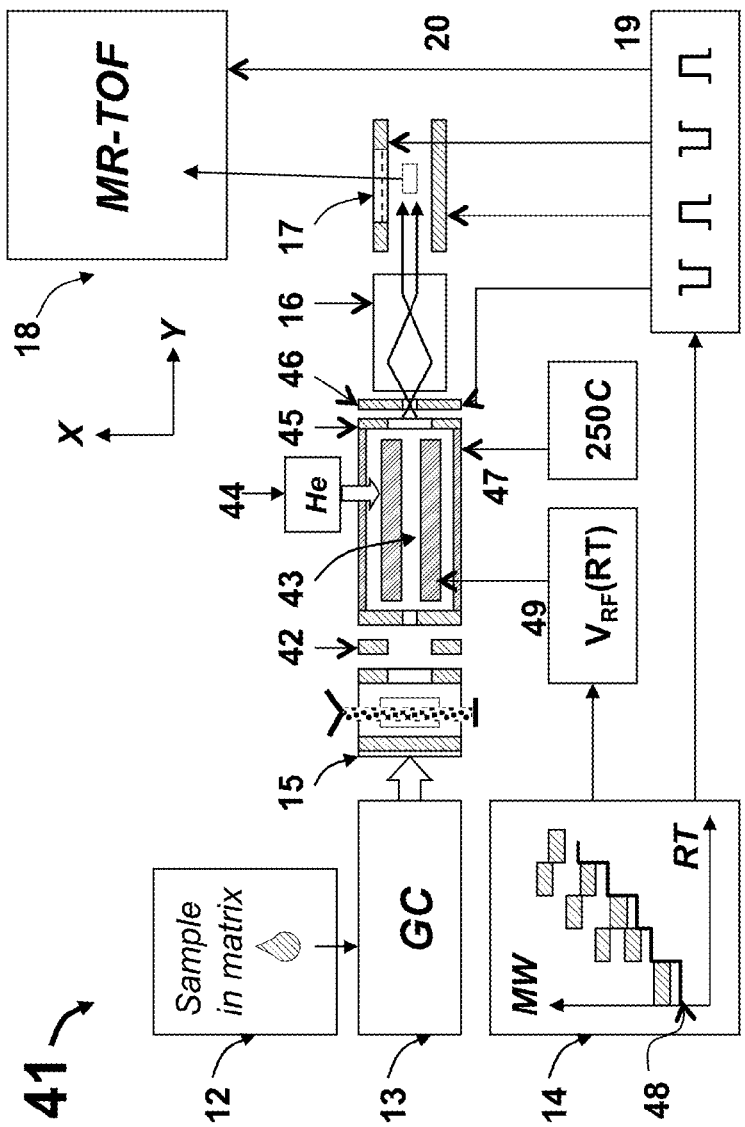
FIG. 4 is a schematic view of an EI-MR-TOF system with ion filtering and ion accumulation in a heated RF only quadrupole.

FIG. 4 provides a schematic view of an EI-MR-TOF system 41 with ion filtering and ion accumulation in RF-only quadrupole (RFQ), according to an implementation. The system 41 comprises an ion optics 42 past EI source 15, a heated RFQ 43 filled with Helium to 1-10 mTor gas pressure via port 44, exit skimmers at electrodes 45 and 46, and RF generator 49. Preferably, an axial DC gradient is arranged within RFQ 43 by using resistive quadrupole rods, e.g. made of ground carbon-filled ceramic resistors (HVP Resistors, US Resistors), and using RF circuit 49 with multiple secondary coils and DC bias supplied via central taps. In experiments we found that it is critical keeping RFQ at elevated temperatures of at least about 250° C. by heating a heat conductive shroud 47. Shroud 47 and RFQ 43 comprise clean materials like metals, glass and ceramics to avoid ion molecular reactions with fumes. Preferably, the heated RFQ may further comprise auxiliary electrodes for providing axial DC field for accelerated ion transfer through the RFQ, described in U.S. Pat. No. 6,111,250. Such auxiliary electrodes may be tapered wedge electrodes (forming wedge in two directions) for improving linearity of axial field. In an implementation, preferably, ion trapping in RFQ 43 may be further improved with auxiliary trapping and pulse electrodes as described in Linear Ion Trap with Axial Ejection as A Source for a TOF MS, ASMS 2005 abstract, Kozlov et.al.

The EI source 15 now operates in continuous mode, thus reducing space charge build up in the source. Ions are focused onto the entrance aperture of the shroud 47, apparently, with nearly unit efficiency at aperture size above 2 mm. DC bias between EI source 15 and RFQ 43 is maintained under about 10 eV to prevent additional ion fragmentation in the RFQ. Moderate (substantially at or between 3-10V) axial DC gradient in RFQ provides rapid ion transfer in the order of about 100-200 us, which does not affect time response in case of using GC×GC with extremely rapid separation. Axial gradient in combination with repelling voltage on either electrode 45 or 46 (preferable), arrange an axial DC trap near the RFQ exit. Ions are periodically extracted by electric pulse on electrode 46. Clock 19 generally synchronizes extraction pulses with OA 17 pulses, such that to admit a relatively narrow mass range (at or between about 20-60 amu) into NR-TOF 18. The admitted mass range is adjusted with GC retention time according to earlier obtained M(RT) map 14 for a particular targeted analysis. The M(RT) map may be obtained in continuous system mode at injection of standards or using standard analysis methodics. Optionally, a precisely equal transmission within the desired mass window may obtained by dithering time delay between RFQ and OA pulses. Optionally, pulse period may be selected shorter than flight time within MR-TOF, while still avoiding signal overlaps due to limited mass window. Alternatively and more preferably, pulse period is extended such that to arrange MR-TOF analysis in so-called zoom mode, wherein for the purpose of enhanced resolution, ions are pulse deflected within MR-TOF for multiple passes. At longer pulse period and due to partial ion sampling from the RFQ, a somewhat lower (at or between about 3-5 mTor) Helium pressure may be used, since ion dampening is controlled by product of gas pressure and time, being approximately 5-10 mtor*ms for at or between about 300-500 amu ions.

As will be shown in experimental section, it can be important to remove low mass ions for the purpose of increasing space charge capacity of the RFQ trapping. The low mass boundary is preferably selected according to curve 48 in the graph 14, so that low mass cut off stays under targeted masses at any particular RT. In an implementation, RFQ is an excellent tool for low mass cut off, particularly at reduced RF frequency. The effectively transferred mass range is known to be proportional to square of RF frequency (if sufficient RF amplitude is provided and the amplitude is limited by low mass boundary) and wide-band RFQ employ at or between about 3-5 MHz frequencies. Contrary to conventional analyses, in targeted analyses there is no need for wide mass range. Thus, RF frequency may be dropped to about 1 MHz for accurately adjustable cut off up to about 1000 amu. Note that RFQ is preferred relative to analytical quadrupoles, which would require much more sophisticated stabilized circuits and would create additional instability of trapped ions.

Alternatively, a limited (e.g., at or between about 10-20 amu) mass band may be selected either by an additional crude quadrupole filter or with a crude time-of-flight filter. The latter may be arranged by accumulating and pulsing ions in EI source 15 as described in WO2012024468 (PEIS), followed by a short linear drift region between EI source 15 and RFQ 43. Such drift space may be arranged by extending the lens 42. Mass selection may be arranged by pulsed admission through the entrance skimmer of the RFQ 43.

As shown in experimental section, the system 41 may be operated in several alternated regimes. Pulsing out narrow mass band of about 20 amu is achieved at pulse duration of at or between about 5-10 us at between about 100-200 fold compression of ion signal. By using wider pulses of at or about 30 us, the compression gain drops to at or between about 10-20, while mass range expands to approximately 200 amu. Full mass range analysis of relatively strong signals, corresponding to at or between about 1 pg-10 ng range, is preferably arranged at continuous RFQ operation at compression gain at or about 1.

The system 41 illustrates advantages of the proposed method over prior art storing EI source (WO2012024468). The ion storage region is transferred from EI source into the RFQ, which allows removal of light ions prior to ion storage, thus dramatically (by several orders of magnitude) reducing space charge limitations at ion storage. The prior art storing EI source is prone to contamination by sample, which affects the ion storage and pulse ejecting regimes. By moving storage region away from the source the system 51 becomes much more stable and rugged.

Figure 5:
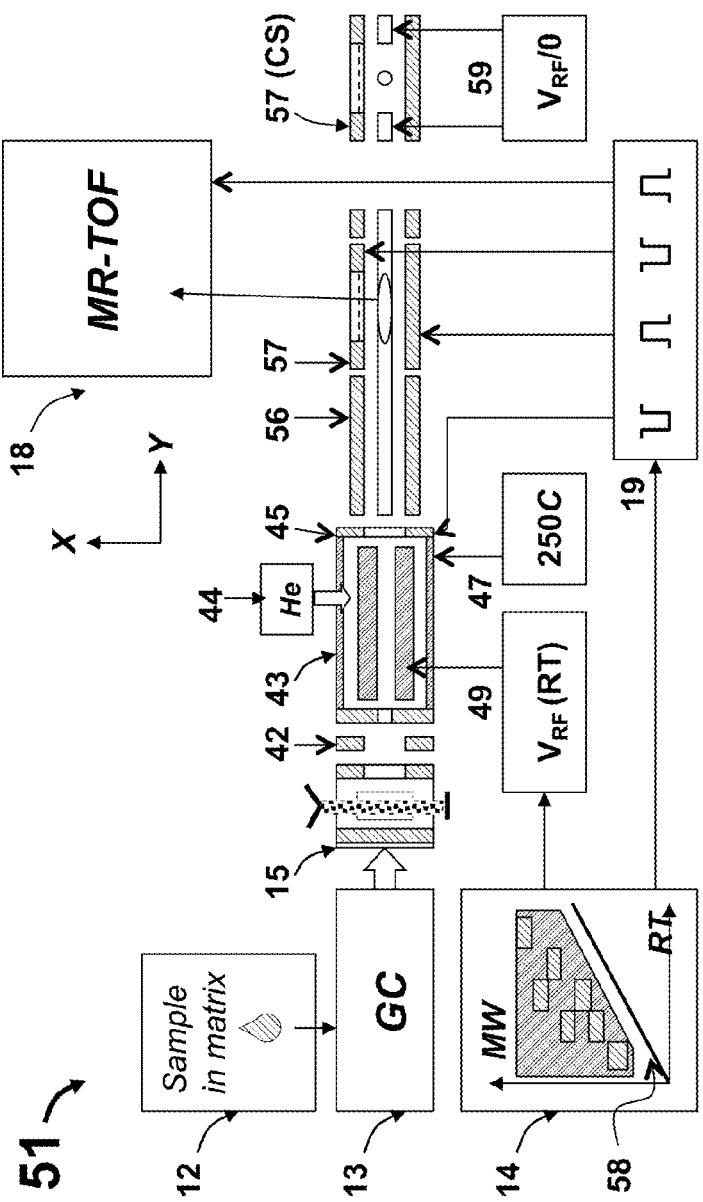
FIG. 5 is a schematic view of an EI-MR-TOF system with ion filtering in a heated RFQ and ion pulsed conversion in a radial ion trap.

FIG. 5 provides a schematic view of an EI-MR-TOF system 51 with ion filtering in a heated RFQ and ion pulsed conversion in a radial ion trap. The upstream portion of system 51 is very similar to one in system 41, except the OA 17 is replaced by a rectilinear ion guide 56 and trap 57 with an additional switching RF supply 59. A cross section of the trap 57(CS) shows that switching RF signal is preferably applied to side electrodes, while DC and pulsed signals are applied to top and bottom electrodes.

In an implementation, system 51 operates as follows. EI source runs continuously, ions are focused by optics 42 onto entrance aperture of heated RFQ 43. RFQ 43 is filled with Helium to gas pressure of approximately 10 mTor. Ion flow is stopped and released in long (at or between about 100 us-1 ms) segments into the guide 56 by applying small amplitude signals to exit RFQ electrode 45. Injected ions are trapped in trap 57 by small DC bias between trap segments. Ions are dampened in Helium at or between about 3-10 mTorr gas pressures and in at or between about 1-2 ms times. Periodically RF signal 59 is switched off and extraction pulses are applied to trap upper and bottom electrodes for ion injection into MR-TOF 18, preferably, via isochronous curved inlet (not shown). In an implementation, low mass ions are filtered out within the RFQ 43. The filtering substantially drops space charge accumulated within the trap 59 and allows prolonged (at or between about 1-2 ms) accumulation of higher mass ions.

Contrary to system 41, the system 51 allows analyzing wider mass ranges, as shown by grey region in the plot 14, however, with the cost of additional system complications, such as rectilinear trap, extra RF supply and curved inlet.

Experimental Tests

The following experiments are for illustration purposes. For experimentally testing the effect of mass filtering onto ion accumulation has been tested in GC-EI-MR-TOF MS system 41, using a closed type ion source 15 an inner diameter ID of 13 mm and a length of 10 mm. For the experiments, a thermo electron emitter 15e provides a stabilizing emission current of 3 mA. Ionization chamber samples a 500 uA current electron beam through 2 mm beam entrance aperture in ionization chamber. A uniform magnet field of 200 Gauss confines electron beam in ionization region. Extraction aperture of ionization chamber has a diameter of about 4 mm and second electrode (e.g., a vacuum sealed extraction electrode) defines an exit aperture having a diameter of about 2 mm. Ionization region receives samples via transfer line from an Agilent 6890N gas chromatograph (available from Agilent Technologies, Inc., 5301 Stevens Creek Boulevard, Santa Clara, Calif. 95051-7201) within a 0.1 to 10 mL/min flow of Helium gas. Most of the experiments correspond to a 1 mL/min helium flow typical for GC micro-columns. For the experiments, ionization chamber floats at +90V relative to ground, and electron energy is selected in a range from between about 20 eV and about 100 eV. Continuously ionized sample is extracted by weak field of several Volts and is focused by two ring electrodes at +85 and +30V into a 2 mm entrance aperture in the heated shroud of RFQ. The RFQ comprises 6 mm resistive rods made of carbon filled ceramic resistors of 200 Ohm (HVP Resistors) and is fed by RF circuit with four secondary coils. An axial gradient of 3-10V is arranged by applying DC bias between rod ends via central taps of secondary coils. RF frequency is 2.3 MHz. The RFQ is heated to 250 C to avoid sample build up and memory effects. At maximum tested amplitude 650V the RFQ removes ions under 150 amu. Ion storage and pulsed ejection are arranged by pulsed signals to exit skimmers at electrodes 45 and 46. Electrode plate 45 has 4 mm diameter and electrode plate 46 −1.5 mm diameter. Between tested schemes it was found that pulsing electrode plate 46 provides a higher compression gain, so the data are presented for only this series of experiments. Typical period of extraction pulses varied from 50 to 650 ms (corresponding to 1000 amu flight time in MR-TOF 18). Typical delay is 30-40 us corresponds to admittance of 300 amu ions. Ion optics 16 is a set of two telescopic lenses also provided with steering electrodes for steering ions into OA. Typical deflection is close to zero illustrating accurate optics alignment. Ion beam divergence is limited by a heated collimator at 150 C temperature and formed by two apertures of 3 and 1.5 mm diameter spaced 80 mm apart.

A 90 eV ion beam enters orthogonal accelerator 17 with a 6 mm effective length of orthogonally sampled ion packets. The ion source, RFQ 43, lens 16, and orthogonal accelerator 17 are all tilted together at an angle of about 4.5 degrees with respect to the Y axis of MR-TOF analyzer 18 for the experiments. The beam is steered back onto the XZ plane past orthogonal accelerator 17. A delay between source extraction pulses and orthogonally accelerating pulses is varied to admit ions of desired mass range, wherein admitted mass range is checked in MR-TOF analyzer 18.

MR-TOF analyzer 18 of FIG. 1 is planar for the experiments and includes two parallel planar ion mirrors each composed of 5 elongated frames. Voltages on electrodes are adjusted to reach a high order of isochronous ion focusing with respect to an initial ion energy, spatial spreads, and angular spreads. A distance between the mirror caps is about 600 mm. The set of periodic lenses enforces ion confinement along the main zigzag trajectory. Ions pass lenses in forward and back Z directions. An overall effective length of the ion path is about 16 m for the experiments. An acceleration voltage of 4 kV is defined by the floating field free region of MR-TOF analyzer 18. The flight time for heaviest ions of 1000 amu can be 600 μs.

In the continuous operation mode, the duty cycle of EI-TOF MS system 41 can be about 0.25% for relatively heavy mass-to-charge ratio (e.g., m/e=1000) and drops proportional to the square root of a smaller ion mass-to-charge ratio. EI-TOF MS system 41 may have a resolution of 45,000-50,000 for relatively heavy ions of 300 amu. In a zoom mode, a lens 20 is pulsed such that ions of interest make second full pass through the analyzer, which doubles both—flight time and resolution.

Figure 6:
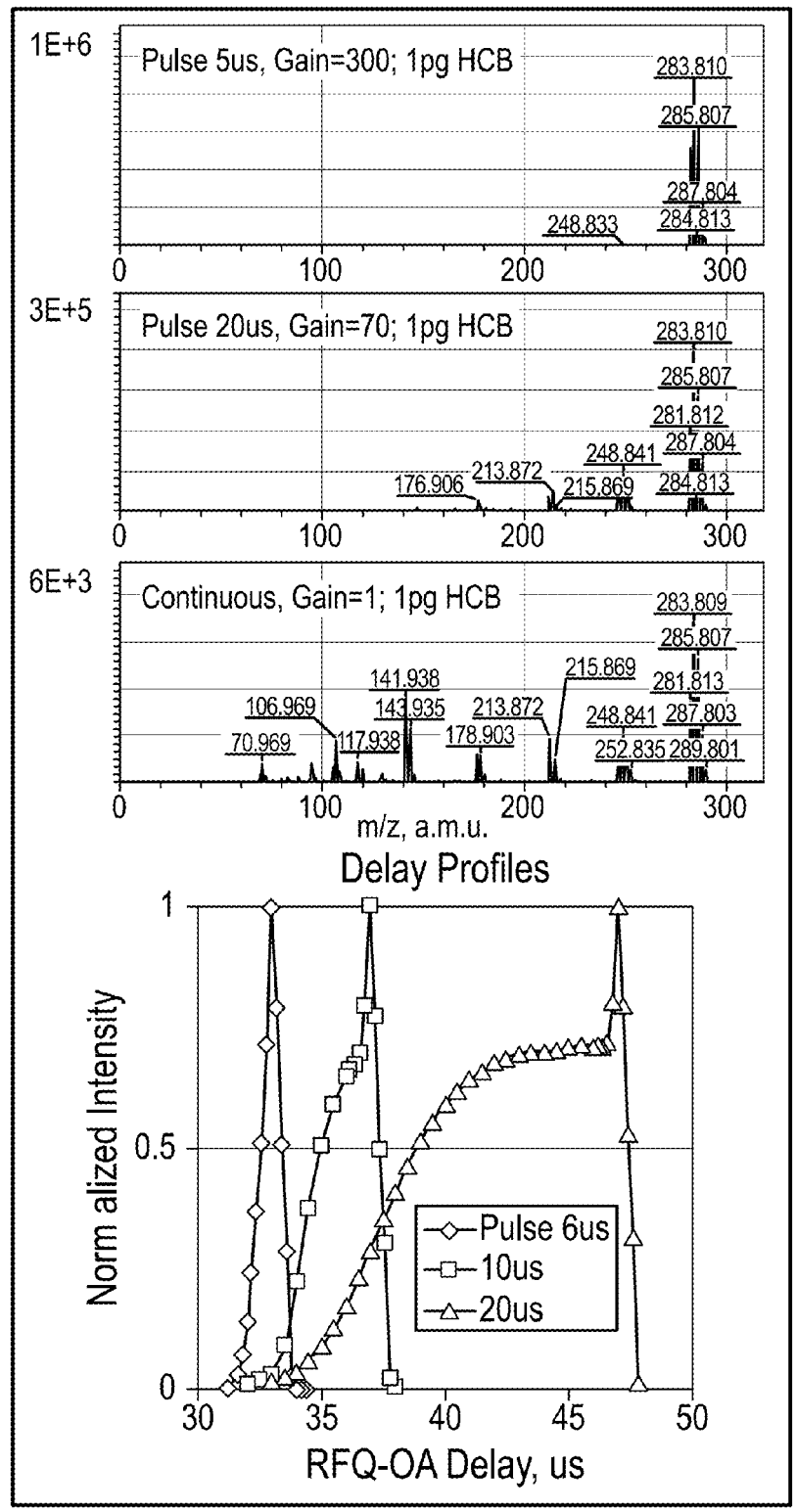
FIG. 6 illustrates measurements of duty cycle past accumulating RFQ verified by time delay profiles.

FIG. 6 illustrates measurements of duty cycle verified by time delay profiles. In a pulse accumulating mode, ions of interest are compressed in time which enhances efficiency of pulsed conversion by 100-200 fold, depending on tuning parameters. For 281 amu ions (corresponding to column bleeding), the profile width is 1.5 us, wherein calculated flight time through 6 mm gap at 90 eV energy is 0.75 us (8 mm/us velocity). Thus experimentally measured duty cycle is 50%.

Figure 7:
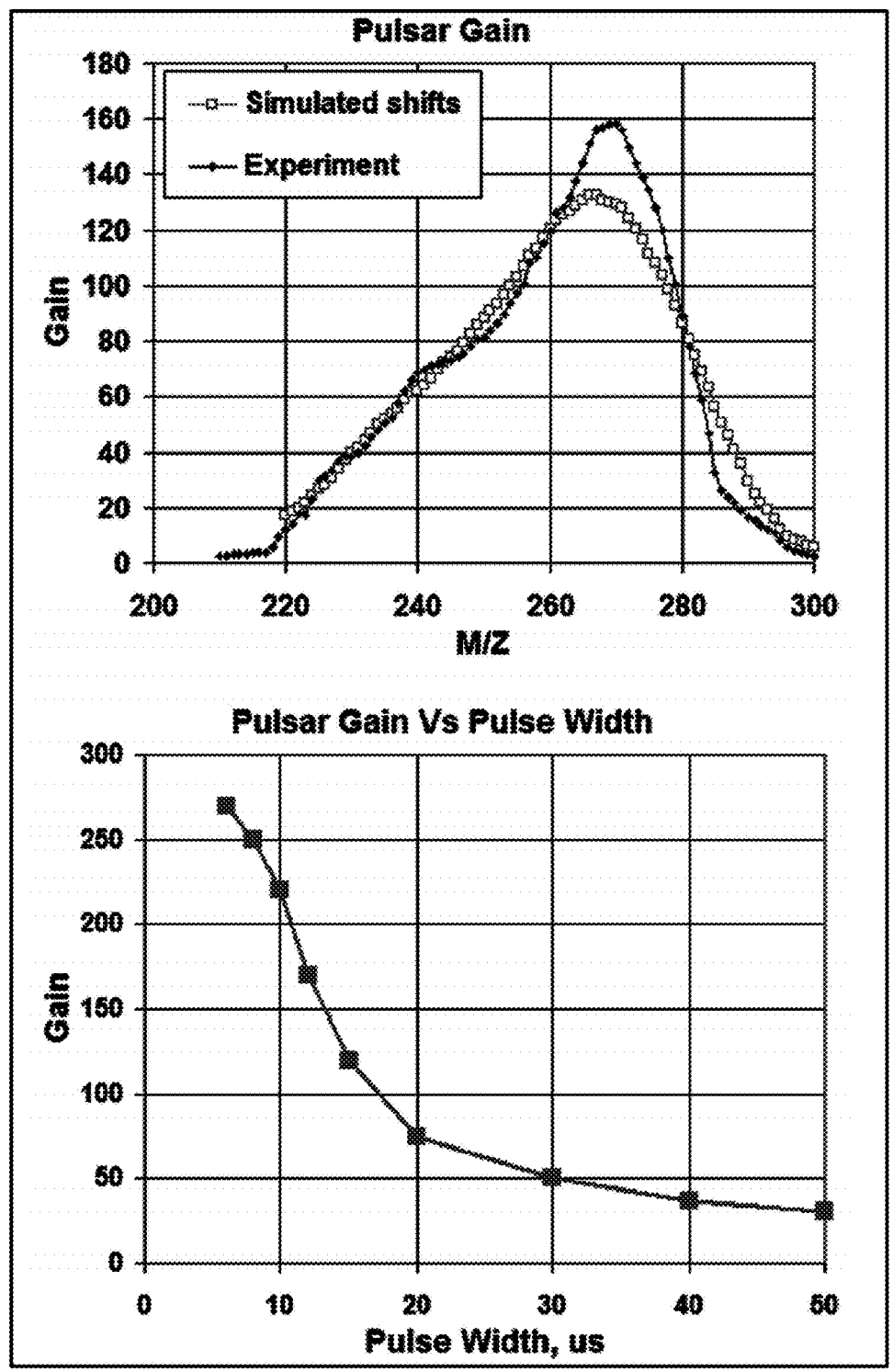
FIG. 7 provides experimental and simulated apparatus function as Pulsar gain Vs m/z.

FIG. 7 illustrates apparatus function as pulsar gain Vs m/z. Gain over 140 is obtained for mass window over 10 amu. A simulated apparatus function is shown if using three alternated delays. Mass window of 20 amu is presented with gain being uniform within 10% at pulsar gain=125.

Figure 8:
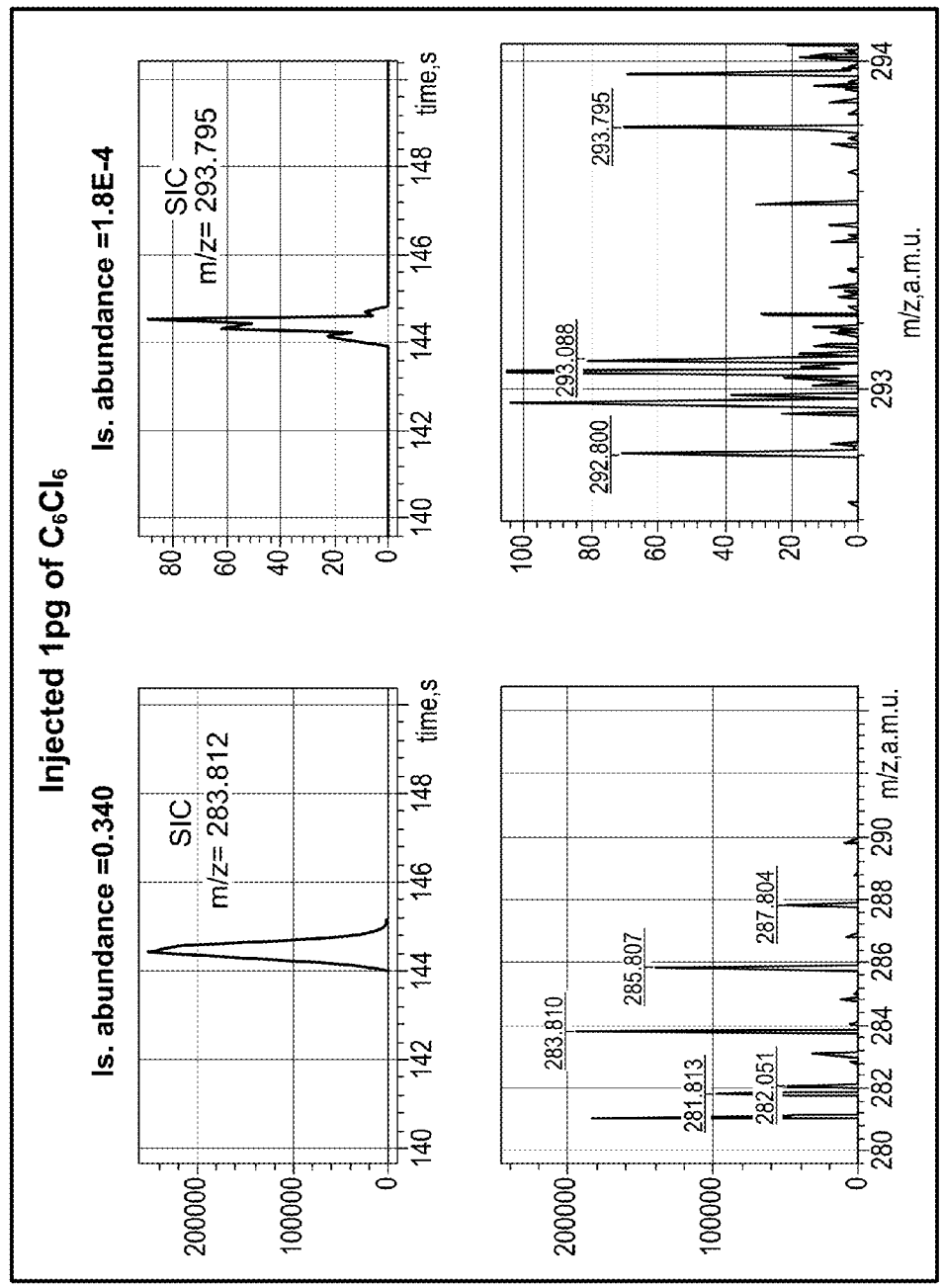
FIG. 8 provides a graphical view of experimental traces of isotopes of HCB obtained from a 1 pg injection of HCB into a GC-EI-MR-TOF MS system.

FIG. 8 illustrates sensitivity of the system 41 obtained at RF amplitude 200V. Sensitivity has been measured with repetitive injections of 100 pg/1 ul hexa-choloro-benzene C6Cl6 (HCB) at 1:100 split corresponding to 1 pg into GC column. Smaller injections were hard to control and were less reproducible. The obtained TIC (total ion current) and SIC (selected ion current) traces for 283.8 ion (major isotope corresponding to ⅓ of total isotope abundance of the isotopic cluster) are shown for pulsed and continuous modes. The total number of detected ions per chromatographic peak was calculated while measuring average number of signal bits per individual ion. While in continuous mode sensitivity is 300-500 ion per major isotope (3000 ions per all HCB peaks), the pulsed mode provides approximately 70,000 to 100,000 ions per major isotope—both at 1 pg injection into GC column. The signal gain is approximately 200 fold. Such sensitivity allows reliable detection of SIC trace for minor 293.8 isotope corresponding to 1/2000 abundance. We conclude that similar trace may be obtained for major isotope at 0.5 fg injection. The instrument provides an unprecedented combination of sensitivity and resolution for targeted analysis. However, when injecting realistic samples containing complex matrix, the sensitivity of pulsed regime was strongly affected.

Figure 9A:
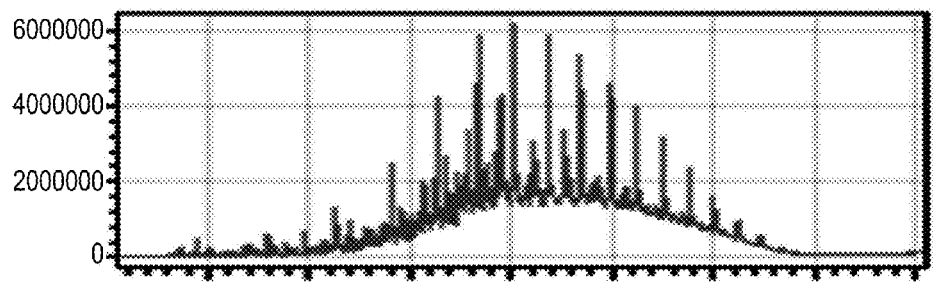
FIGS. 9A-9C provides a graphical view of experimental traces of isotopes of HCB obtained from a 1 pg injection of HCB and of 1 microgram of diesel matrix into a GC-EI-MR-TOF MS system at low RF amplitude in RFQ—200V at 2 MHz, corresponding to low mass cut of M*=50 amu.
Figure 9B:
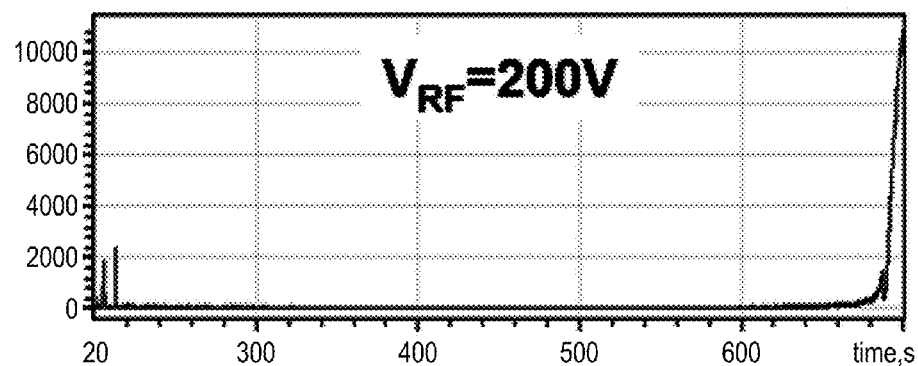
Figure 9C:
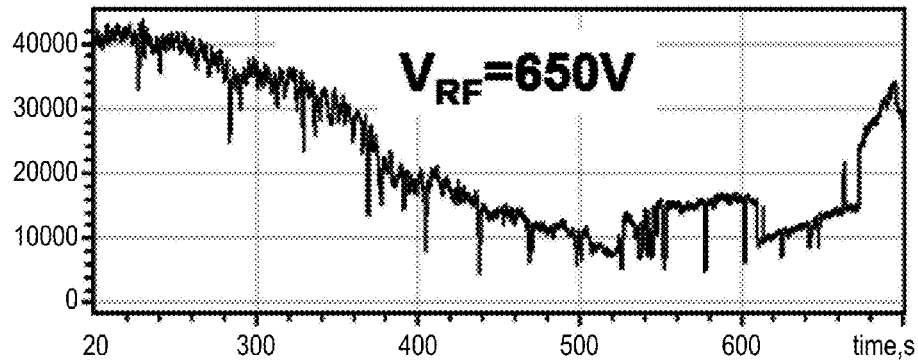

FIGS. 9A, 9B and 9C illustrate the effect of low mass cut off onto recovery of sensitivity in the pulsed mode. FIG. 9A shows an exemplary TIC profile acquired in continuous MR-TOF mode for 1 ug diesel loaded into GC column. Maximal peaks correspond to 10 ng/sec sample flux into the source. FIG. 9B shows SIC for 264 amu (PFTBA peak) at 1 ug diesel load when system 41 was operated in pulsed mode and RFQ is set to 200V. Signal of PFTBA peak vanishes at sample load approaching 1 ng/sec. FIG. 9C shows SIC for 264 amu (PFTBA peak) at 1 ug diesel load when system 41 was operated in pulsed mode and RFQ is set to 650V. Signal of PFTBA peak has some variations during diesel elution. However, similar signal modulations are observed in continuous operation mode. Thus, those variations are caused by saturation of continuous source rather than by saturation of space charge at RFQ storage. The modulations are known to disappear when using larger apertures in the EI source.

Figure 10:
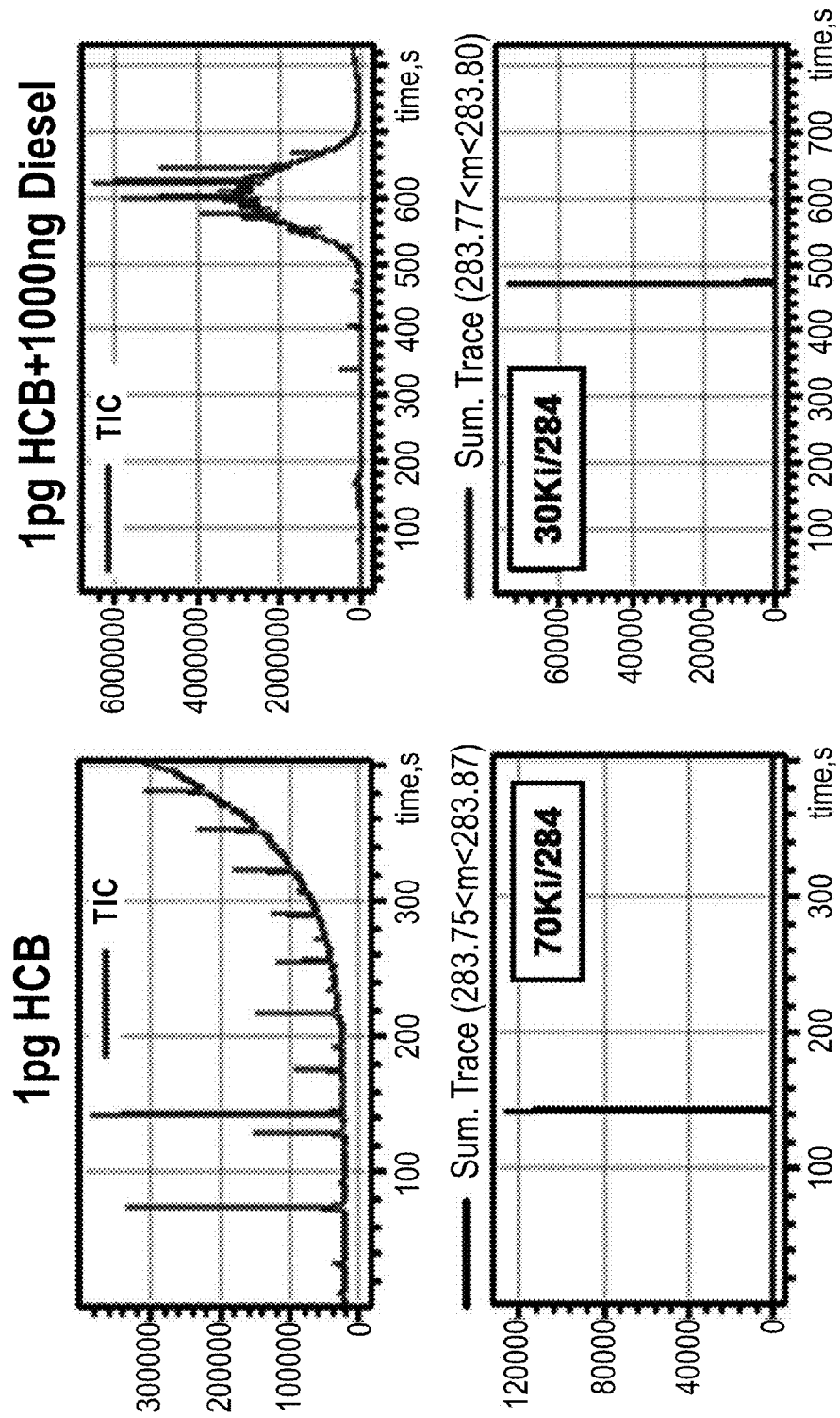
FIG. 10 provides a graphical view of experimental traces of isotopes of HCB obtained from a 1 pg injection of HCB and of 1 microgram of diesel matrix into a GC-EI-MR-TOF MS system at high RF amplitude in RFQ—600V at 2 MHz, corresponding to low mass cut of M*=150 amu.

FIG. 10 presents an example of simultaneous co-injection of 1 pg HCB with 1 ug diesel, sensitivity is lower than in case of pure HCB, but still provides approximately 50,000 ions per 283.8 isotope per GC peak at 1 pg HCB injection. Thus femtogram detection is proved at presence of 1 ug matrix, i.e. detectable ratio of concentrations is 1 ppb.

Figure 11:
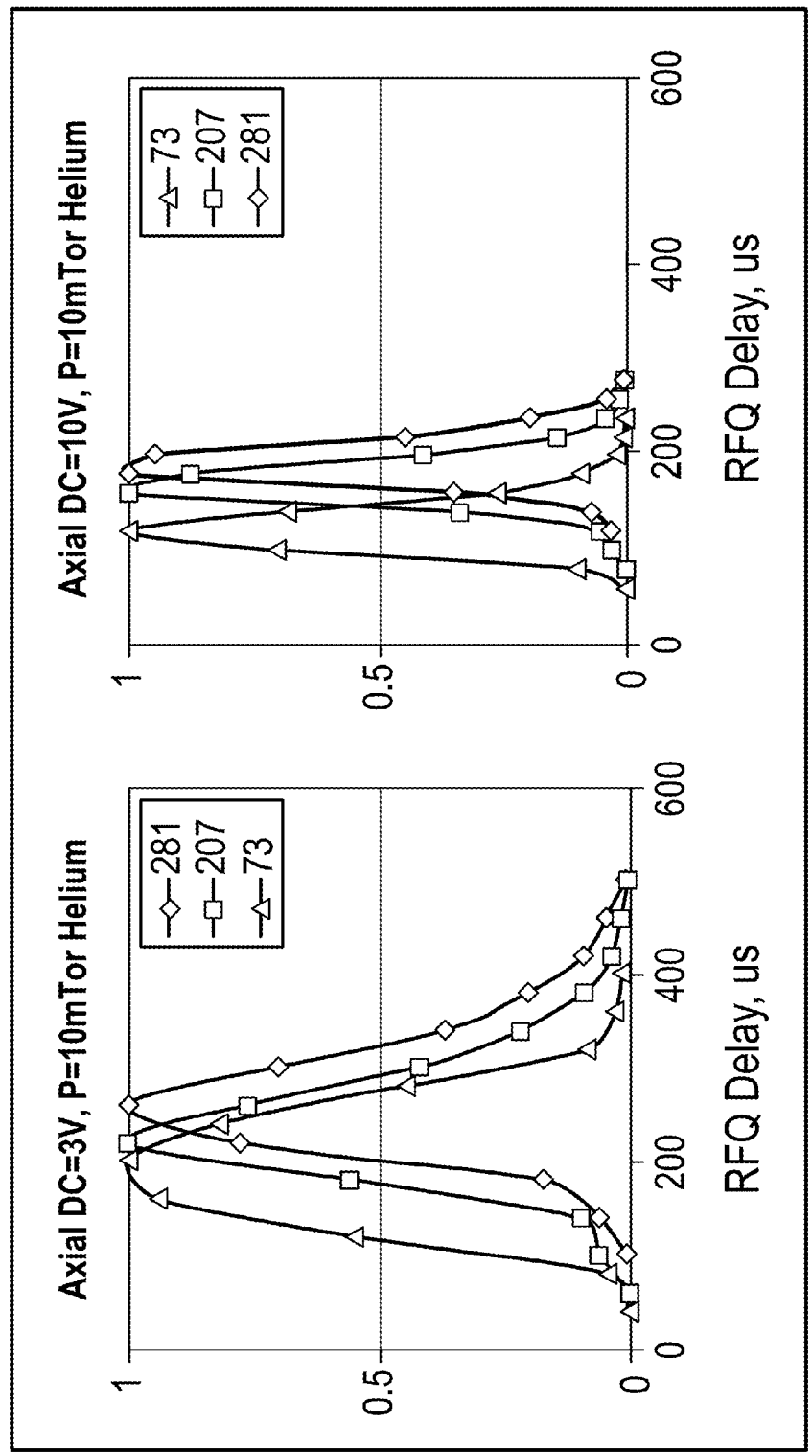
FIG. 11 provides a graphical view of time profiles showing speed of ion propagation within the RFQ.

FIG. 11 presents time profile of ion propagation within the RFQ 43 at 10 mtor Helium pressure and at 5V DC gradient. Ion pulse at the RFQ entrance is formed by pulsing an ion optics in front of the RFQ. The pulse delay is 100-200 us (depending on ion mass), while pulse width is about 50 us. Thus, ion propagation through RFQ would not affect any fastest separation in GCxGC.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method of targeted mass spectrometric analysis for a sample comprising:
    establishing a map of target mass as a function of retention times RT for chromatographic separation;
    injecting and chromatographically separating the sample;
    ionizing the sample;
    removing low mass ions smaller than the target mass M(RT) by
        low mass filtering in a radio-frequency field only quadrupole (RFQ) ion guide,
        heating the RFQ above 200 degC, and
        arranging an axial DC field configured to accelerate and to control ion axial velocity and to reduce ion molecular reactions;
    ion accumulating and pulsed ejecting via the radio-frequency only quadrupole (RFQ); and
    mass analyzing in multi-reflecting time-of-flight mass spectrometer MR-TOF MS.

2. The method of claim 1, further comprising:
    synchronized orthogonal pulsed acceleration.

3. The method of claim 1, wherein said step of chromatographic separation is arranged at large volume injections above about 1 uL of solvent.

4. The method of claim 1, wherein said step of chromatographic separation is arranged at Helium flow from at or substantially between 0.5 mL/min to 2 mL/min.

5. The method of claim 1, wherein said step of chromatographic separation is arranged at Helium flow from 2 mL/min to 20 mL/min and wherein the method further comprises:
    splitting the eluent in a differentially pumped stage prior to ionizing the sample.

6. The method of claim 1, wherein said step of ionization comprises one step selected from the group consisting of: (i) electron impact ionization (EI); (ii) chemical ionization (CI); (iii) photo-chemical ionization (APPI); (iv) atmospheric pressure chemical ionization (APCI); (v) Electrospray (ESI); (vi) SESI; (vii) conditioned glow discharge ionization (GD); and (viii) using either positive or negative ion mode in above ionization methods.

7. The method of claim 1, wherein said steps of low mass filtering and ion accumulation in RF only quadrupole further comprises filling said RFQ with Helium gas at 1 to 10 mTor gas pressure range.

8. The method of claim 1, wherein said step of mass spectrometric analysis in MR-TOF further comprises the step of reverting ion motion by side lenses in order to double flight path and MR-TOF resolution.

9. A method of targeted mass spectrometric analysis for a sample comprising:
    establishing a map of target mass as a function of retention times RT for chromatographic separation;
    injecting and chromatographically separating the sample;
    ionizing the sample;
    removing low mass ions smaller than the target mass M(RT) by
        low mass filtering in a linear radio frequency ion trap and
        heating the ion trap above 200 degC;
    ion accumulating and pulsed ejecting via the ion trap; and
    mass analyzing in multi-reflecting time-of-flight mass spectrometer MR-TOF MS.

10. The method of claim 9, wherein removing low mass ions further comprises arranging an axial DC field configured to accelerate and to control ion axial velocity and to reduce ion molecular reactions.

11. The method of claim 9, wherein removing low mass ions further comprises filling said ion trap with Helium gas at 1 to 10 mTor gas pressure range.

* * * * *